United States Patent
Spiegelhalter

[11] Patent Number: 6,013,068
[45] Date of Patent: Jan. 11, 2000

[54] VARIABLE LUMEN CATHETER

[76] Inventor: Judith A. Spiegelhalter, 1122 Keystone Dr., Jupiter, Fla. 33458

[21] Appl. No.: 09/123,623

[22] Filed: Jul. 28, 1998

[51] Int. Cl.[7] .................................................. A61M 25/00
[52] U.S. Cl. .......................................... 604/523; 604/264
[58] Field of Search ............................... 604/523, 93, 264

[56] References Cited

U.S. PATENT DOCUMENTS 5,149,330  9/1992  Brightbill .............................. 604/283

*Primary Examiner*—Wynn Wood Coggins
*Assistant Examiner*—Kevin C. Sirmons
*Attorney, Agent, or Firm*—McHale & Slavin, PA

[57] ABSTRACT

The present invention is a convertible catheter which is of a size and construction so as to enable it to be inserted by a medical technician and is designed so as to convert the site of ingress from a single lumen configuration to a multilumen configuration without necessitating removal of the first catheter.

9 Claims, 1 Drawing Sheet

VARIABLE LUMEN CATHETER

FIELD OF THE INVENTION

This invention relates to the field of multilumen catheters, and most particularly relates to catheters which are readily convertible from single to multilumen configurations and are easily insertable by nurses or emergency medical technicians.

BACKGROUND OF THE INVENTION

Upon initiation of treatment, emergency medical technicians must often seek to administer intravenous fluids, especially to an individual who has sustained a trauma. This requires the initiation of a means of ingress to the patient's bloodstream, and is often hampered by injuries such as lacerations, scrapes, burns, etc. which limit the number of usable sites. Intravenous fluid administration devices often include a holder carrying a plastic catheter and a removable needle cannula passing through the distal tip of the catheter for inserting the needle and catheter through the skin and into a body vessel such as a vein. After successfully performing the venopuncture, the needle is removed and a source of infusion liquid such as glucose, blood, saline solution or other liquid is supplied to the holder to supply the infusion liquid to the vein.

As particular situations progress, critical response to divergent patient needs is of the utmost importance. Although it may be necessary to instill a variety of fluids and medications in varying amounts, the ability of the technician to accomplish this is often impaired by a paucity of viable infusion sites. For example, a patient's blood supply may be dangerously diminished, requiring rapid infusion of large volumes of replacement blood or plasma. This will require a relatively large bore catheter. Subsequently, conditions may arise requiring the continued supply of moderate amounts of intravenous fluid, while simultaneously requiring medications such as heart rhythm medications, seizure control medications, medications designed to control blood pressure fluctuations, etc. in order to maintain physiological stability. Instilling these medications often requires multiple means of ingress while maintaining separate and distinct flow paths so that intermixing of medications, and possible interactions thereof, are prevented.

It is known to form catheters with extremely large bores and to adapt these catheters for single or multiple lumens configurations. This enables the insertion of intravenous fluids, blood, drugs and/or the extraction of blood, via the same entry point, and without intermixing of the fluids. The problem which exists, is that these catheters are of such a large bore that they require surgical implantation by a physician in an emergency room or operating room. A sterile environment is required for their insertion, and a local anesthetic is generally administered to facilitate the procedure.

U.S. Pat. No. 5,149,330 to Brightbill describes such a catheter which is capable of being converted from a single lumen catheter into a multilumen catheter. The Brightbill device is designed for use during a surgical procedure where a large bore catheter is initially required to be surgically inserted so as to provide a means of ingress for large quantities of blood or other fluids. After completion of the surgery, Brightbill supplies a multilumen insert which is mateable with the large bore catheter and is capable of converting this large bore catheter to function as a multilumen catheter without the necessity of removal of the large bore device. The first elongated large-bore device of Brightbill is described as being 13 gauge or larger, e.g. having an outer diameter of at least 0.092 inches. The second catheter is described as having an internal diameter on the order of 0.047" or 16 gauge while the internal lumens are 18 gauge. Such devices have great utility in an operating room environment but are not suitable for emergency use by a nurse or emergency medical technician.

Unfortunately, the presently available catheters which are suitable for field usage do not allow for convertibility from large to small size or from single to multilumen configurations.

Thus, what is lacking in the art is a convertible catheter which is of a size and construction so as to enable it to be inserted by a medical technician and is designed so as to convert the site of ingress from a single lumen configuration to a multilumen configuration without necessitating removal of the first catheter.

SUMMARY OF THE INVENTION

In accordance with the present invention, a multilumen intravascular catheter is provided wherein the lumen are of a relatively small bore size for facilitating their introduction into the vascular system of a patient. Initially, a single lumen plastic catheter, on the order of 18–20 gauge and having a removable needle cannula therein, is inserted into the vein of a patient. After completion of the venopuncture and removal of the needle cannula, a multilumen catheter in the range of 22–24 gauge is insertable into the 18–20 gauge catheter. The multilumen catheter is of a size and taper adapted to frictionally and sealingly engage the inner wall of the single lumen catheter, thereby providing a means by which the nurse or technician may safely instill multiple fluids or medicaments via the same puncture site. Alternatively, if an emergency arises where large volumes of blood or some other intravenous fluid become necessary, the multilumen adapter is easily removable thereby providing a larger bore catheter without requiring additional venopuncture.

The multilumen catheter contains a plurality of spaced-apart side opening discharge ports at its distal end, each of which are in communication with a different annular region of the catheter and thereby in fluid communication with different fluid sources. This construction allows for the discharge of differing fluids into the patient's bloodstream without the danger of intermixing. It is extremely important to guard against intermixing certain fluids and/or drugs since untoward reactions may occur, e.g. precipitation, crystallization, coagulation or premature reaction between blood and medications in vitro as opposed to in vivo.

The catheter assembly of the present invention further includes a manifold assembly having a proximal end and a distal end, the proximal end containing a plurality of ports for fluid communication with various sources of intravenous fluids or medicaments. The plurality of ports are in further communication with fluidically distinct annular regions of the multilumen catheter, whose proximal end is sealingly engaged within the manifold assembly. The plurality of ports may be oriented at an angle relative to the longitudinal axis of the manifold assembly, or they may be collinear therewith.

A particularly preferred embodiment utilizes a double lumen catheter wherein a first port is collinear with a central proximal opening of the manifold assembly thereby fluidly communicating with a first of said lumens. A second port transverses the cylindrical manifold assembly at an angle of approximately 45° and thereby intersects and fluidly communicates with the second lumen. This construction enables rapid input of differing fluids to either of the lumens, thus enabling effective patient treatment while utilizing a minimum number of venopuncture sites.

It is an objective of the present invention to provide a small bore catheter assembly having a multilumen configuration.

It is a further objective of this invention to provide a catheter assembly which enables noninvasive conversion of a venopuncture site from a single to a multiple lumen catheter.

It is yet another objective of this invention to provide a catheter assembly and method of use whereby nursing staff or emergency medical personnel are able to effect conversion from single to multilumen configurations.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE ILLUSTRATED EMBODIMENTS

Figure 1:
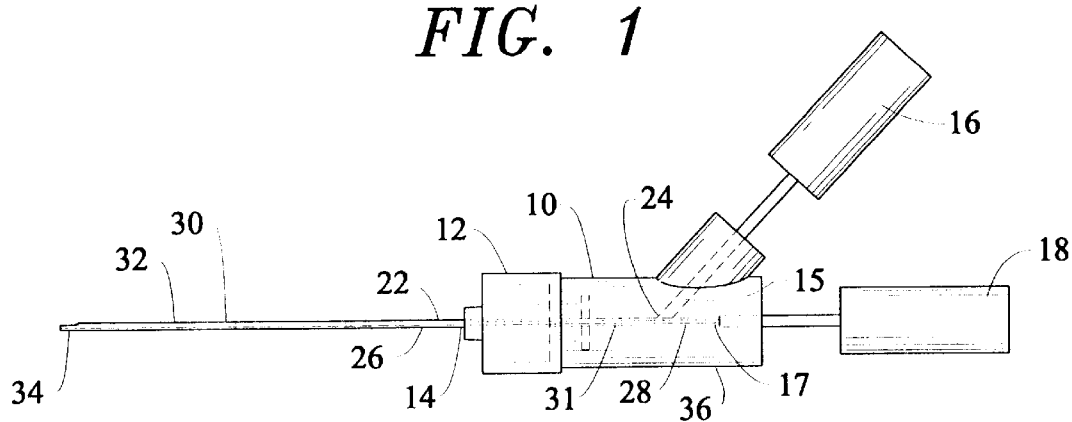
FIG. 1 is a perspective view of a dual lumen catheter assembly.

Referring now to FIG. 1, the multilumen catheter assembly 10 is shown. For purposes of this discussion, a dual lumen catheter is depicted, although the invention contemplates the use of alternative embodiments containing 3 or more lumens. Manifold assembly 12 fluidly and sealingly engages a dual lumen catheter 14 containing two fluidically distinct lumens 22 and 26, at a proximal end 31, thereof. The manifold assembly contains plural passages 15 and 17, each providing for distinct fluidic communication with one of said lumens. Fluid coupling assemblies 16 and 18 are in sealing engagement with the plural passages of the manifold assembly at its proximal end 36. Coupling assembly 16 intersects outer lumen 22 through an opening 24; corresponding coupling assembly 18 communicates with inner lumen 26 via opening 28. The coupling assemblies are adapted to receive and sealingly engage a hollow needle-like member or similar coupling device which carries fluid or medicaments from their source. The dual lumen catheter distal end 30 terminates in spaced apart side-opening discharge ports 32 and 34 which provide for separate and distinct transport of disparate fluids and medicaments while avoiding the dangers inherent in intermixing. In use, the distal end 30 of the multilumen catheter is frictionally and sealingly engaged within a previously inserted single lumen catheter of appropriate size. The single lumen catheter is of standard configuration and is not a part of the instant invention. In practice, the single lumen catheter is of a size range on the order of 18–20 gauge. The dual lumen catheter is selected to fit within the appropriate single lumen catheter and is of a size range on the order of 22–24 gauge.

Figure 2:
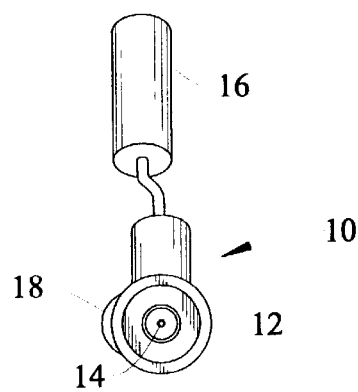
FIG. 2 is a distal end-view of a dual lumen catheter assembly.

Referring to FIG. 2, wherein like reference numerals indicate like parts as above, a distal end-view of the catheter assembly 10 shows the sealing engagement of the manifold assembly 12 with the dual lumen catheter 14. The engagement of coupling assemblies 16 and 18 with the manifold assembly is shown. In use, the distal tip of the catheter is frictionally and sealingly engaged within a single lumen catheter of appropriate size whereby transport of disparate fluids and medicaments is made possible by insertion thereof in fluid coupling assemblies 16 and 18 which provide fluid communication thereto via the manifold assembly 12.

Figure 3:
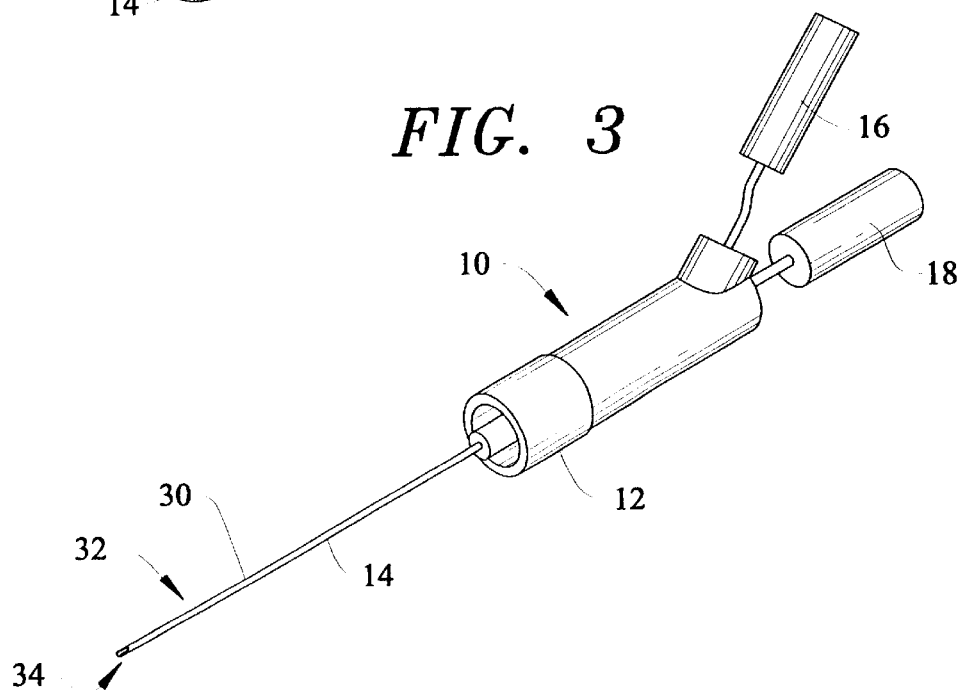
FIG. 3 is a side-view of a dual lumen catheter assembly.

With reference to FIG. 3, wherein like reference numerals indicate like parts as above, a perspective view of the device is shown. Catheter assembly 10 is shown comprising manifold assembly 12, dual lumen catheter 14 and coupling assemblies 16 and 18. Disparate fluids and/or medicaments travel toward the distal end 30 of the dual lumen catheter 14 via fluid coupling assemblies 16 and 18, and follow separate and distinct paths, finally arriving at spaced apart side-opening discharge ports 32 and 34, whereby safe and effective distribution is achieved.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

I claim:

1. A multilumen catheter assembly adapted for frictional and sealing engagement within a single lumen catheter consisting of:

a multilumen catheter containing fluidically distinct plural lumens and having a proximal end and a distal end;

said multilumen catheter distal end having spaced apart side-opening discharge ports constructed and arranged so as to provide for separate and distinct delivery of disparate fluids and medicaments via said plural lumens;

a manifold assembly fluidly and sealingly engaging the multilumen catheter at the proximal end thereof;

said assembly further containing plural fluid passages for fluidic communication with said plural lumens; and plural fluid coupling assemblies fluidly engaging said plural fluid passages, each said passage being in distinct fluidic communication with a particular lumen of said multilumen catheter and in sealing engagement therewith;

whereby said multilumen catheter separately and distinctly delivers disparate treating fluids and medicaments to the bloodstream of a patient through said spaced apart side-opening discharge ports.

2. The multilumen catheter assembly according to claim 1 wherein said multilumen catheter is within a size range of 22–24 gauge and is adapted to frictionally and sealingly engage a single lumen catheter within a size range of 18–20 gauge.

3. The multilumen catheter assembly according to claim 1 wherein the multilumen catheter is a dual lumen catheter.

4. A multilumen catheter assembly for use by nursing and emergency medical personnel and adapted for frictional and sealing engagement within a single lumen catheter consisting of:

a multilumen catheter containing fluidically distinct plural lumens and having a proximal end and a distal end;

said multilumen catheter distal end having spaced apart side-opening discharge ports constructed and arranged so as to provide for separate and distinct delivery of disparate fluids and medicaments via said plural lumens;

a manifold assembly fluidly and sealingly engaging the multilumen catheter at the proximal end thereof;

said assembly further containing plural fluid passages for fluidic communication with said plural lumens; and plural fluid coupling assemblies fluidly engaging said plural fluid passages, each said passage being in distinct fluidic communication with a particular lumen of said multilumen catheter and in sealing engagement therewith;

whereby the multilumen catheter assembly is constructed and arranged so as to enable nursing and emergency medical personnel to provide separate and distinct deliver of disparate treating fluids and medicaments to the bloodstream of a patient through said spaced apart side-opening discharge ports.

5. The multilumen catheter assembly according to claim 4 wherein said multilumen catheter is within a size range of 22–24 gauge and is adapted to frictionally and sealingly engage a single lumen catheter within a size range of 18–20 gauge.

6. The multilumen catheter assembly according to claim 4 wherein the multilumen catheter is a dual lumen catheter.

7. A noninvasive method to provide for the conversion, by nursing and emergency medical personnel, of a single lumen catheter to a multilumen catheter assembly consisting essentially of:

providing a multilumen catheter containing fluidically distinct plural lumens and having a proximal end and a distal end and wherein said multilumen catheter distal end has spaced apart side-opening discharge ports constructed and arranged so as to provide for separate and distinct delivery of disparate fluids and medicaments via said plural lumens;

providing a manifold assembly fluidly and sealingly engaging the multilumen catheter at the proximal end thereof and further containing plural fluid passages for fluidic communication with said plural lumens; and providing plural fluid coupling assemblies engaging said plural fluid passages, each said passage being in distinct fluidic communication with a particular lumen of said multilumen catheter and in sealing engagement therewith;

whereby nursing and emergency medical personnel may frictionally and sealingly engage said multilumen catheter assembly within a single lumen catheter so as to provide a multilumen catheter assembly that separately and distinctly delivers disparate treating fluids and medicaments to the bloodstream of a patient through said spaced apart side-opening discharge ports.

8. The noninvasive method according to claim 7 wherein said multilumen catheter is within a size range of 22–24 gauge and is adapted to frictionally and sealingly engage a single lumen catheter within a size range of 18–20 gauge.

9. The noninvasive method according to claim 7 wherein the multilumen catheter is a dual lumen catheter.

* * * * *